United States Patent [19]

Kawakami et al.

[11] Patent Number: 5,262,531
[45] Date of Patent: Nov. 16, 1993

[54] PROCESS FOR PREPARING 2'-DEOXY-β-ADENOSINE

[75] Inventors: Hiroshi Kawakami; Hajime Matsushita, both of Yokohama; Hajima Yoshikoshi, Tokyo; Kazuo Itoh, Tokyo; Yoshitake Naoi, Tokyo, all of Japan

[73] Assignees: Japan Tobacco, Inc.; Yuki Gosei Kogyo, Co. Ltd., Japan

[21] Appl. No.: 373,467

[22] Filed: Jun. 30, 1989

[30] Foreign Application Priority Data

Jul. 5, 1988 [JP] Japan .................. 63-166063

[51] Int. Cl.$^5$ ........................... C07H 1/00
[52] U.S. Cl. .................. 536/27.11; 536/27.12; 536/27.13; 536/27.6
[58] Field of Search ............. 536/23, 24, 26, 124, 536/27.11, 27.12, 27.13, 27.6; 544/244, 243

[56] References Cited

U.S. PATENT DOCUMENTS

| | | | |
|---|---|---|---|
| 3,480,613 | 11/1969 | Walton et al. | 536/27.23 |
| 3,501,456 | 3/1970 | Shen et al. | 536/27.23 |
| 3,721,664 | 3/1973 | Hoffer | 536/27.12 |
| 3,748,320 | 7/1973 | Vorbruggen et al. | 536/233 |
| 3,868,373 | 2/1975 | Hoffer | 544/229 |
| 4,209,613 | 6/1980 | Vorbroggen | 536/27.23 |
| 4,760,137 | 7/1988 | Robins et al. | 536/27.11 |
| 4,782,142 | 1/1988 | Bardos et al. | 536/26.8 |
| 4,929,723 | 5/1990 | Frescos | 536/28.53 |
| 5,047,519 | 9/1991 | Hobbs, Jr. et al. | 536/24 |
| 5,142,051 | 8/1992 | Holy et al. | 544/244 |

FOREIGN PATENT DOCUMENTS

| | | |
|---|---|---|
| 173059 | 3/1986 | European Pat. Off. . |
| 175004 | 3/1986 | European Pat. Off. . |
| 300765 | 1/1989 | European Pat. Off. . |
| 0350293 | 1/1990 | European Pat. Off. . |
| 1919307 | 1/1971 | Fed. Rep. of Germany . |
| 1070413 | 6/1967 | United Kingdom ......... 536/23 |
| 1386584 | 2/1975 | United Kingdom ......... 536/26 |
| 1601020 | 10/1981 | United Kingdom . |

OTHER PUBLICATIONS

Nucleic Acid Research, vol. 12, No. 2, pp. 1179–1192, 1984.
Int. J. of Methods in Synthetic Organic Chemistry, No. 7, pp. 329–343, 1970.
Chemical Abstracts, vol. 86, No. 15, Apr. 11, 1977, p. 547, Abstract No. 106950a, Itoh et al "Synthesic Studies of potential antimetabolites".
J. Am. Chem. Soc. vol. 106, 1984, pp. 6379–6382. Kazimierczuk et al "Synthesis of 2'-deoxytubercidin--glycosylation procedure".
J. Am. Chem. Soc. vol. 105, 1988, pp. 4059–4065; M. J. Robins et al "Nucleic Acid Related Compounds".
Seela, F., et al., "2-Amino-7-(β-D-arabinofuranosyl)-pyrrolo[2,3-d]pyrimidin-4(3H-one. Synthesis of ara-7-Deazaguanosine via Phase Transfer Glycosylation", J. Org. Chem. (1982), vol. 47, pp. 226–230.
The Synthesis of 2'-Deoxyadenosine via Stereospecific Coupling Reaction; Kawakami et al; Chemistry Letters; pp. 237–238, 1989.
European Search Report EP 89 30 6834.
Journal of the American Chem. Society vol. 106, 1984 pp. 6379–6382 Z. Kazimierczuk et al "Synthesis of 2'--deoxyadenosine and related 2'-deoxynucleosides etc.".
Chemical Abstracts, vol. 90 No. 11, Mar. 12, 1979, p. 658 A. Holy "L-Adenosine. A Stereospecific synthesis of α-riboniucleosides from 2-0-p-tolylsulfonyl etc.".
Journal of the American Chem. Society, vol. 105, No. 12, Jun. 15, 1983, pp. 4059–4065 M. J. Robins et al "Nucleic Acid related compounds. 42. A general procedure etc.".
Chemical Abstracts, vol. 98 No. 17, Apr. 25, 1983, H. Griengl "Cyclic aldehyde derivatives as alkylating reagents. I: Acyclo and azaacyclo analogs etc.".

*Primary Examiner*—Johnnie R. Brown
*Assistant Examiner*—James O. Wilson
*Attorney, Agent, or Firm*—Beveridge, DeGrandi, Weilacher & Young

[57] ABSTRACT

2'-deoxy-β-adenosine can be industrially and easily obtained without using expensive or dangerous materials by the process of the present invention, which comprises the steps of: preparing a salt of adenine from adenine, allowing to condense the salt with a derivative of pentofuranose to isolate a derivative of adenine, and then eliminating the protecting groups.

7 Claims, No Drawings

PROCESS FOR PREPARING 2'-DEOXY-β-ADENOSINE

BACKGROUND OF THE INVENTION

The present invention relates to a process for preparing 2'-deoxy-β-adenosine having the following formula [I]:

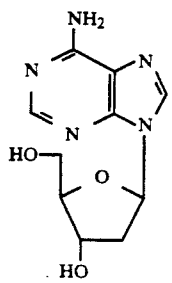

2'-deoxy-β-adenosine obtained by the present invention is a raw material of the compound which is useful as a medicine, and it is a constituent of deoxyribonucleic acid, which is a gene. Consequently, the demand for 2'-deoxy-β-adenosine is increasing with the advance of genetic engineering in recent years.

Conventionally 2'-deoxy-β-adenosine is prepared from natural deoxyribonucleic acid by decomposing it with enzymes. However, such process is not fit for industrial preparation, because the raw material is restricted in the resources thereof.

The following processes as "chemical synthesis" are known:

(1) Derivatives of adenine are allowed to condense with derivatives of 2-deoxy-D-erythro-pentofuranose to obtain an equivalent mixture of anomers and then β-type compound is separated. [Biochimica et Biophysica Acta, 145, 221(1967)].

(2) Hydroxyl group of 2-position of adenosine as a raw material is eliminated to obtain 2'-deoxy-β-adenosine. [Journal of American Chemical Society, 105, 4059 (1983); Journal of Organic Chemistry, 47, 485 (1982)].

In the process of the above (1), it is complicated to separate β-type compound desired from a mixture of anomers, and in the process of the above (2), poisonous tin compounds have to be used. Therefore, these processes are not industrial.

Recently, synthesis of 2'-deoxy-β-adenosine has been reported that sodium salt of 6-chloropurine derivative and 1-chloro-2-deoxy-3,5-di-O-p-toluoyl-α-D-erythro-pentofuranose are subjected to β-selective condensation. [Journal of American Chemical Society, 106, 6379 (1984); TOKKYO-KOKAI-KOHO (18-month Publication of Unexamined Patent Application) SHOWA 61(1986)-106594].

In this process, there are defects that: (1) 6-chloropurine derivative used as a raw material is expensive; (2) sodium hydride used in preparation of a sodium salt is dangerous; (3) in substitution of a chloro group with an amino group, heating and pressurization are required. Consequently, conventional processes are not industrially preferable.

SUMMARY OF THE INVENTION

The inventors studied a process for preparing selectively and efficiently β-type compound having the formula [I] as mentioned above, and found that compound [I] can be obtained by allowing to condense Compound [III] with Compound [IV] without catalyst to obtain β-type compound with a selectivity of 90% or more, and eliminating a protecting group of purified Compound [II].

Namely, the present invention relates to a process for preparing 2'-deoxy-β-adenosine characterized in that a salt of adenine having the general formula [IV]:

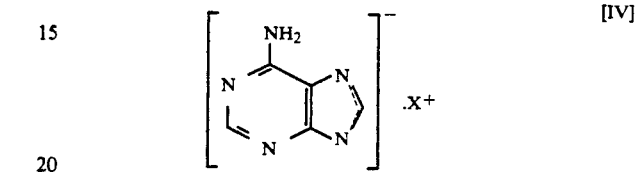

(wherein $X^+$ is a cation) is prepared from adenine having the formula [V]:

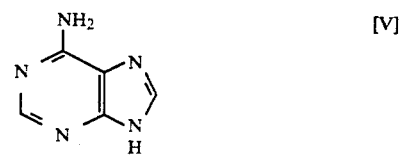

and the salt obtained is allowed to condense with a derivative of 1-chloro-2-deoxy-α-D-erythro-pentofuranose having the general formula [III]:

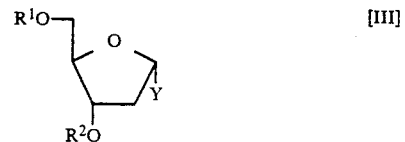

(wherein $R^1$ and $R^2$ are a protecting group of a hydroxyl group and Y is a halogen) to isolate a derivative of 9-(2-deoxy-β-D-erythro-pentofuranosyl)adenine having the general formula [II]:

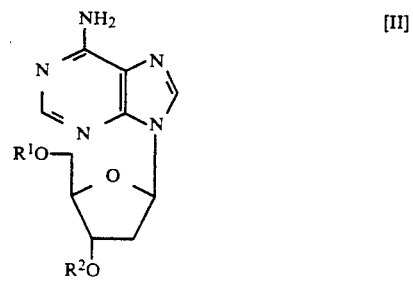

(wherein $R^1$ and $R^2$ are as above defined) and then the protecting groups are eliminated to obtain 2'-deoxy-β-adenosine having the formula [I]:

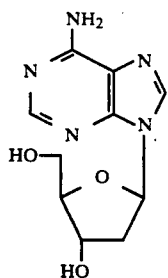
(I)

For protecting two hydroxyl groups of Compound [III], the following groups are employed, which are used as a protecting group of saccharides; aralkyl group such as benzyl group and trityl group; acyl group such as acetyl group, propionyl group, pivaloyl group and benzoyl group; alkyloxy carbonyl group such as ethoxy-carbonyl group; aryloxycarbonyl group such as phenoxycarbonyl group. These protecting groups are not limited to the groups as mentioned above.

These protecting groups may have an alkyl group, a halogen atom, a nitro group, or an alkoxyl group as a substituent, when the protecting groups have a phenyl group.

A cation of Compound [IV] is a metal cation such as sodium, potassium and lithium, and an ammonium cation such as tetraethylammonium. Sodium ion is preferably used.

The sodium salt can be obtained by the reaction of Compound [V] with sodium hydroxide or sodium alcoholate in water or alcohol at room temperatures within usually 30 minutes. The sodium salt is stable and easy to handle.

Condensation of Compound [IV] with Compound [III] is carried out in a solvent having moderate polarity such as aceton, acetonitrile, 1,2-dichloroethane, dichloromethane, diethyl ether, 1,2-methoxyethane, tetrahydrofuran and ethyl acetate at room temperatures, and it is usually completed within 19 hours. Acetone is preferably used.

When the reaction mixture contains trace amounts of position isomers, the mixture of α- and β-type compounds produced is isolated from the reaction mixture by an appropriate means such as column chromatography, and then purified by recrystallization to obtain pure β-type compound [II], and further the protecting groups are eliminated by hydroysis, alcoholysis, ammonolysis or the like to obtain 2'-deoxy-β-adenosine [I].

As mentioned above, 2'-deoxy-β-adenosine can be obtained in a high yield by the process of the present invention without using expensive or dengerous raw materials.

EXPLANATION OF THE PREFERRED EMBODIMENTS

The present invention will be illustrated by the following examples, but the present invention is not restricted thereto.

(1) Sodium Salt of Adenine 0.54 g (10 mmol) of sodium methylate was added to a suspension of 1.4 g (10 mmol) of adenine [V] in 50 ml of methanol, and the mixture was stirred at room temperatures for 30 minutes.

After the crystals dissolved completely, the solvent was distilled away under reduced pressure, and the white crystals obtained were dried under reduced pressure to obtain 1.6 g of the captioned compound. Yield 100%

$^1$H-NMR (D$_2$O): δ8.03 (s, 1H), 7.96 (s, H).

(2)
9-(2-deoxy-3,5-di-O-p-toluoyl-β-D-erythro-pentofuranosyl) adenine 0.45 g (1.3 mmol) of dry-powdered 1-chloro-2-deoxy-3,5-di-O-p-toluoyl-D-erythro-pentofuranose was added to a suspension of 0.40 g (2.5 mmol) of sodium salt of adenine in 25 ml of absolute acetone, and the mixture was stirred at room temperatures for 19 hours.

After the reaction was completed, the reaction solution was poured into an aqueous solution of sodium chloride, and the reaction mixture was extracted with methylene chloride. The organic layer was dried over anhydrous magnesium sulfate, and then the solvent was distillated away under reduced pressure.

The residue obtained was purified by silicagel column chromatography with a mixture of methylene chloride and acetone (volume ratio of methylene chloride to acetone=50:50) as a solvent.

The captioned compound was crystallized from ethyl acetate, to obtain 0.29 g of the captioned compound, which was crystals having ½ molecule of ethyl acetate. Yield 43%.

m.p.: 168°–169° C.

$^1$H-NMR(CDCl$_3$): δ8.33(s, 1H, H-8), 7.98 (s, 1H, H-2), 7.97 (d, J=9.3 Hz, 2H, aromatic-H), 7.91 (d, J=8.2 Hz, 2H, aromatic-H), 7.28 (d, J=8.8 Hz, 2H, aromatic-H), 7.22 (d, J=8.2 Hz, 2H, aromatic-H), 6.54 (dd, J=8.4 and 5.8 Hz, 1H, H-1'), 5.81 (dt, J=6.4 and 2.2 Hz, 1H, H-3'), 5.73 (br., 2H, NH$_2$), 4.76 (dd, J=11.8 and 3.8 Hz, 1H, H-5'), 4.67 (dd, J=11.8 and 4.4 Hz, 1H, H-5''), 4.64 (m, 1H, H-4'), 3.11 (ddd, J=14.3 and 8.2 and 6.2 Hz, 1H, H-2'), 2.83 (ddd, J=14.2 and 5.8 and 2.0 Hz, 1H, H-2''), 2.44 (s, 3H, CH$_3$), 2.40 (s, 3H, CH$_3$).

(3) 2'-deoxy-β-adenosine [I]

20 ml of ammonia water was added to a solution of 0.97 g (1.8 mmol) of 9-(2-deoxy-3,5-di-O-p-toluoyl-β-D-erythro-pentofuranosyl)adenine in 100 ml of methanol, and the mixture was stirred at room temperatures for 24 hours.

After the reaction was completed, the reaction solution was concentrated under reduced pressure, and the residue obtained was dissolved in water and washed twice with chloroform.

The aqueous layer was concentrated under reduced pressure, and the crystals obtained were recrystallized from water to obtain 0.44 g of monohydrate of the captioned compound. Yield 89%.

m.p.: 189°–190° C.

(m.p. disclosed in literatures: 187°–189° C.).

$^1$H-NMR (CD$_3$OD): δ8.31 (s, 1H, H-8), 8.18 (s, 1H, H-2), 6.43 (dd, J=8.0 and 5.9 Hz, 1H, H-1'), 4.58 (dt, J=5.8 and 2.7 Hz, 1H, H-3'), 4.07 (q, J=2.9 Hz, 1H, H-4'), 3.85 (dd, J=12.4 and 2.9 Hz, 1H, H-5'), 3.75 (dd, J=12.3 and 3.4 Hz, 1H, H-5''), 2.81 (ddd, J=13.5 and 7.9 and 5.7 Hz, 1H, H-2'), 2.41 (ddd, J=13.4 and 6.0 and 2.8 Hz, 1H, H-2'').

We claim:

1. A process for preparing 2'-deoxy-β-adenosine having the formula (I):

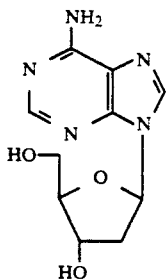

comprising reacting an adenine having the formula (V):

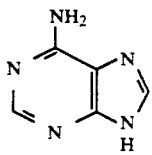

with an alkali metal alcoholate or alkali metal hydroxide to form a salt of adenine having the formula (IV):

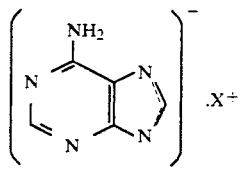

wherein $X^+$ is a cation selected from the group consisting of sodium, potassium and lithium, obtaining a crystallized salt of adenine having the formula IV, condensing said crystallized salt with a derivative of 1-chloro-2-deoxy-α-D-erythro-pentofuranose having the formula (III):

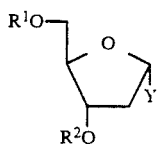

wherein $R^1$ and $R^2$ are a protecting group of a hydroxy group selected from a group consisting of aralkyl, acyl, alkyloxy carbonyl and aryloxy carbonyl, and Y is Cl, in a solvent having moderate polarity, to isolate a derivative of 9-(2-deoxy-β-D-erythropentofuranosyl) adenine having the formula (II):

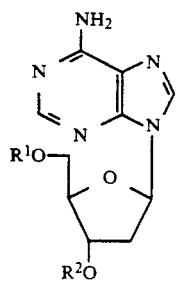

wherein $R^1$ and $R^2$ are as above defined, followed by eliminating the protecting groups; wherein said process occurs in the absence of a catalyst.

2. The process according to claim 1 wherein the cation is sodium.

3. The process according to claim 1, wherein said solvent is selected from the group consisting of acetone, acetonitrile, 1,2-dichloroethane, dichloromethane, diethyl ether, 1,2-methoxyethane, tetrahydrofuran and ethyl acetate; wherein said solvent is the sole solvent utilized in said process.

4. The process according to claim 3, wherein said solvent is acetone.

5. The process according to claim 1, consisting essentially of reacting an adenine having the formula (V):

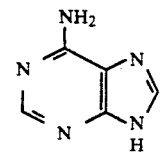

with an alkali metal alcoholate or alkali metal hydroxide to form a salt of adenine having the formula (IV):

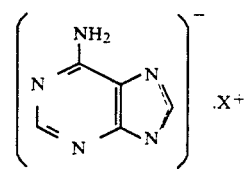

wherein $X^+$ is a cation selected form the group consisting of sodium, potassium or lithium, obtaining a crystallized salt of adenine having the formula IV, condensing said crystallized salt with a derivative of 1-chloro-2-deoxy-α-D-erythro-pentofuranose having the formula (III):

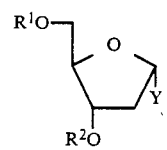

wherein $R^1$ and $R^2$ are a protecting group of a hydroxy group selected from a group consisting of aralkyl, acyl, alkyloxy carbonyl and aryloxy carbonyl, and Y is Cl, in a solvent having moderate polarity, to isolate a derivative of 9-(2-deoxy-β-D-erythropentofuranosyl) adenine having the formula (II):

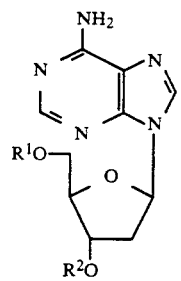

wherein $R^1$ and $R^2$ are as above defined, followed by eliminating the protecting groups.

6. The process according to claim 1, wherein $R^1$ and $R^2$ are toluoyl.

7. The process according to claim 1, wherein said protecting group is selected from the group consisting of benzy, trityl, acetyl, propionyl, pivaloyl, benzoyl, ethoxy-carbonyl, and phenoxycarbony.

* * * * *